United States Patent [19]

Croset et al.

[11] 4,272,350
[45] Jun. 9, 1981

[54] ELECTROCHEMICAL SENSOR FOR MEASURING CONCENTRATIONS OF SPECIES IN A FLUID MIXTURE, OF THE TYPE COMPRISING A PARTIAL-PRESSURE INTERNAL REFERENCE ELECTRODE

[75] Inventors: Michel Croset; Gonzalo Velasco, both of Paris, France

[73] Assignee: Thomson-CSF, Paris, France

[21] Appl. No.: 102,915

[22] Filed: Dec. 12, 1979

[30] Foreign Application Priority Data

Dec. 12, 1978 [FR] France ................................ 78 34880

[51] Int. Cl.³ .......................................... G01N 27/46
[52] U.S. Cl. .................................................. 204/195 S
[58] Field of Search ............................. 204/1 S, 195 S

[56] References Cited

U.S. PATENT DOCUMENTS

| 3,719,564 | 3/1973 | Lilly et al. ........................ 204/1 S |
| 3,914,169 | 10/1975 | Horowitz ........................ 204/195 S |
| 3,915,830 | 10/1975 | Isenberg ........................ 204/195 S |
| 3,974,054 | 8/1976 | Poolman et al. ................. 204/195 S |
| 4,040,929 | 8/1977 | Bauer et al. ..................... 204/195 S |
| 4,107,019 | 8/1978 | Takao et al. ..................... 204/195 S |
| 4,126,532 | 11/1978 | Takao et al. ..................... 204/195 S |
| 4,171,253 | 10/1979 | Nolan et al. ..................... 204/195 S |

FOREIGN PATENT DOCUMENTS 2758835 7/1979 Fed. Rep. of Germany ....... 204/195 S
2350598 2/1977 France .

OTHER PUBLICATIONS

Schoonman, "J. Electrochem. Soc.: Electrochemical Science and Technology", vol. 123, No. 12, pp. 1772–1775, Dec. 1976.
Kennedy et al., "J. Electrochem. Soc.: Electrochemical Science and Technology", vol. 123, No. 1, pp. 10–14, Jan. 1976.

Primary Examiner—T. Tung
Attorney, Agent, or Firm—Oblon, Fisher, Spivak, McClelland & Maier

[57] ABSTRACT

The electrochemical sensor for measuring concentrations of species in a fluid mixture is of the type comprising a partial-pressure internal reference electrode constituted by a system in which a metal is combined with an oxide of said metal. One face of the reference electrode is in contact with a solid electrolyte. An inert protective coating deposited on all the other faces of the electrode is impervious to the species which are present in the fluid mixture.

7 Claims, 15 Drawing Figures

ELECTROCHEMICAL SENSOR FOR MEASURING CONCENTRATIONS OF SPECIES IN A FLUID MIXTURE, OF THE TYPE COMPRISING A PARTIAL-PRESSURE INTERNAL REFERENCE ELECTRODE

This invention relates to electrochemical sensors for measuring the concentrations of species in a fluid mixture and in particular in a gas.

Figure 1:
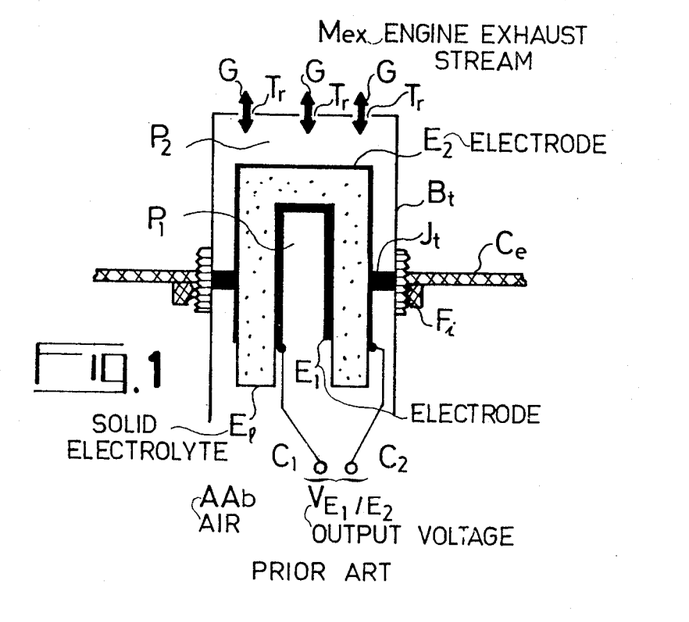
FIG. 1 is an electrochemical sensor of the prior art, of the so-called "glove finger" type.

One of the well-known families of sensors for the measurement of partial gas pressures operates on the principle of a concentration cell. The gas mixture which is to be analyzed and consists, for example, of oxygen and an inert gas is present within a compartment 2 and separated from a reference medium 1 by the wall of a solid electrolyte $E_l$, each face of which is adapted to carry an electrode designated respectively by the references $E_2$-$E_1$.

As is well known, the equations governing these sensors are:

at the electrodes/electrolyte interfaces:

(1)

the voltage then developed between the electrodes is given by the Nernst law:

$$V_{E1/E2} = \frac{RT}{4F} \ln \frac{P_1}{P_2} \quad (2)$$

with
R = ideal gas constant = 8.314 (mole·°K.)
F = Faraday number = 96490
T = absolute temperature in degrees Kelvin
$P_1$ and $P_2$ = partial pressures of media 1 and 2 within compartments 1 and 2.

Should the mixture be reactive and consist, for example, of a mixture $O_2$ + CO and if the electrode acts as a catalyst in the reaction of these gases, the following reaction takes place:

$$2CO + O_2 \rightleftharpoons 2CO_2 \quad (3)$$

and finally, if the combustion is complete until a reversible thermodynamic equilibrium is attained, the following relation is established:

(4)

where K(T) is a coefficient of equilibrium which depends on the temperature and $|CO|$, $|O^2|^{\frac{1}{2}}$, $|CO^2|$ are the partial pressures of carbon monoxide, oxygen and carbon dioxide gas.

A first approach in the construction of sensors of the prior art makes use of ambient air as a reference medium or at least of a reservoir containing a suitable gas. The most common construction is the so-called "glove finger" design in which the central portion is constituted by a solid electrolyte whilst the inner and outer faces are covered with electrodes. The interior of the "glove finger" usually communicates with the atmosphere and the exterior communicates with the medium to be analyzed. Since the electrolyte usually serves as a mechanical support, an electrolyte of thick consistency is employed.

Another approach proposes the use of means for combining the electrode function and the reference-medium function. To this end, use is accordingly made of an electrode based on a combination of the type: M-Mx where M is a metal and X is a halogen to be detected (for example M-MO in the case of detection of oxygen). One improvement which has also been proposed in this approach consists of sensors fabricated in accordance with the thin-film technique. Among other advantages, these two types of construction make it possible to overcome to a partial extent the disturbing effects of temperature on the response curve of the sensors. It is in fact clear from equations (2) and (4) that the value of $V_{E1/E2}$ is doubly dependent on the "temperature" parameter. According to the tables of heat of formation of the M-MX pair, a suitable choice in fact makes is possible to provide partial compensation for the two temperature-sensitive terms.

These two approaches have a common characteristic in that the reference medium $P_1$ is separated from the medium $P_2$ to be analyzed essentially by the solid electrolyte, whether this latter is in the form of a thick wall and in most cases of ceramic material (as is usually the case with "glove finger" sensors) or whether it is in the form of a thin film. This represents a certain number of disadvantages and, as is often the case, especially in applications in which the absolute pressure of the medium to be analyzed is of high value. Among these disadvantages can be mentioned the following:

the porosity of the wall of solid electrolyte with respect to the gas to be analyzed, thus resulting in early degradation of the reference medium;

the difficulty involved in ensuring leak-tightness between the analysis and reference compartments and the resultant potential danger of leakages;

thermal and mechanical stresses (especially those arising from vibrations) which result in crack formation and impaired reliability of the sensor.

A third approach has already been proposed in the case of analysis of reactive media. This approach consists in making use of two different metals for the fabrication of electrodes. For example, one electrode is fabricated from non-catalytic material and the other electrode is fabricated from catalytic material. Thus a reference medium can accordingly be dispensed with. The differential pressure effect is reproduced artificially by selective activity of the two electrodes on the same medium, namely the medium to be analyzed. Aside from the difficulty presented by the choice of materials which are really suitable for the fabrication of the two electrodes, sensors of this type are not free from all the disadvantages which have been mentioned. In particular, the two electrodes and the electrolyte are subject to aggressive action of the medium to be analyzed. Some of these designs also require an auxiliary electric power supply.

It should finally be noted that this approach cannot be employed in the case of analysis of fluid media in thermodynamic equilibrium in which the effect of dissymmetry of operation of electrodes, whether catalytic or not, no longer serves any useful purpose.

In the following description, consideration will be given only to analysis of the relative concentration of carbon monoxide and oxygen contained in a fluid mixture and more particularly in the exhaust gases of an internal combustion engine. This example is given solely by way of illustration and is not intended to limit the scope of the invention.

In order to overcome the disadvantages indicated in the foregoing, the invention is therefore directed to an electrochemical sensor for measuring concentrations of species contained in a fluid mixture and comprising an electrochemical cell having a flat structure. Said cell is constituted by a first partial-pressure internal reference electrode, one face of said electrode being either wholly or partly in contact with a solid electrolyte which is an ionic conductor for one of the species of said fluid mixture or for an ion which is capable of reacting with said species. A second electrode of the electrochemical cell communicates with the fluid mixture to be analyzed, one face of said second electrode being either wholly or partly in contact with the solid electrolyte. An inert envelope serves to protect all the other faces of the first electrode and is impervious to the species which are present in the fluid mixture.

FIG. 1 is a schematic presentation of a sensor according to a first approach of the prior art. The sensor comprises an electrochemical cell in the form of a "glove finger" composed of a first electrode $E_1$ in contact with the reference medium $P_1$ which communicates with the atmosphere AAb, of a solid electrolyte $E_I$ and a second electrode $E_2$ which is in contact with the medium $P_2$ to be analyzed. As a rule, this medium is not constituted directly by the fluid mixture to be analyzed. In point of fact, the fluid mixture may be subjected to very rapid motion causing transport of solid residues which would result in damage to the sensor within a very short time. This is the case in particular if the fluid mixture to be analyzed is the exhaust gas of an internal combustion engine. A sensor is usually placed within the exhaust pipe through which the combustion residues are discharged to the atmosphere. Such residues consist of gases, especially carbon monoxide, water vapor, oxygen and carbon dioxide gas, and of different solid particles. In this application, the sensor is intended to analyze any deviation with respect to stoichiometry as defined by reaction (3). It is realized that, in addition to chemical and kinetic aggression, the sensor is subjected to very considerable variations in pressure and temperature. These effects are attenuated by placing the electrochemical cell $E_2$-$E_I$-$E_1$ within a casing $B_t$ which is open to the medium Mex to be analyzed through calibrated holes $T_r$ or baffles which limit the exchange of gas G between the medium Mex to be analyzed and the interior of the sensor. So-called "test samples" are taken and tend to produce a continuous analyzing operation. It still holds true that the sensor has many weak points including the seals $J_t$ within the sensor and (as recalled earlier) the electrochemical cell itself. Seals $F_i$ which serve to secure the casing are less critical since the analysis would not be disturbed if a leak were to develop at this level.

Figure 2:
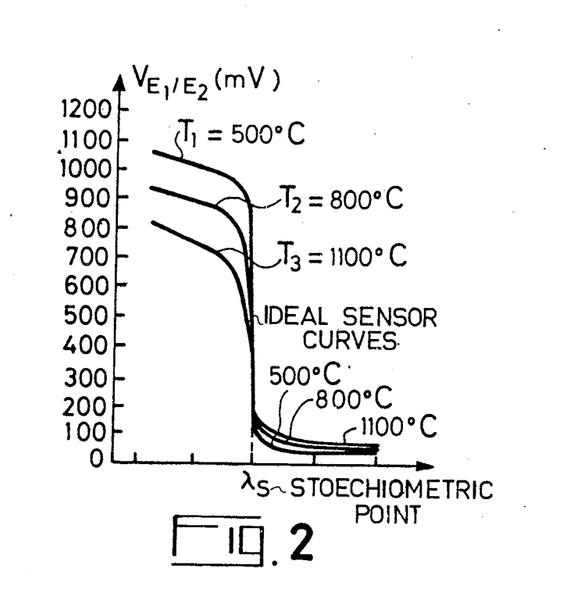
FIG. 2 is a set of response curves of the sensor of FIG. 1 in the case of a reactive fluid mixture.

Moreover, the response of this type of sensor is highly dependent on temperature by virtue of equations (2) and (4) as has also been mentioned earlier. FIG. 2 shows a set of curves giving the temperature parameters (500° C., 800° C., 1100° C.) of the difference in interelectrode potential ($V_{E1/E2}$) as a function of the ratio of relative concentrations of oxygen and carbon monoxide. It is possible as a rule to utilize only the central portion of these curves, namely the portion in which they practically coincide or in which they are less dependent on temperature variations. The abrupt inflexion of the curve in which the abscissa $\lambda_S$ represents the stoichiometry of the reaction as defined by the relation:

$$|CO| = \tfrac{1}{2}|O_2| \tag{5}$$

is detected.

Even under these conditions, it is more advantageous to provide the possibility of limiting the effects of temperature, the more so as the curves of FIG. 2 represent the response of an ideal sensor. All the limitations mentioned in the foregoing result in aging of the sensor, one effect among others being the collapse of the response curve as represented by curve A in FIG. 3 in respect of a given temperature of 800° C. Inflexion becomes progressively less marked and increasingly difficult to detect with accuracy.

Finally, by reason of the insufficient catalytic activity of the majority of sensors of the prior art and of mechanisms which will be discussed further below, curve inflexion does not take place exactly at stoichiometry $\lambda_S$ but at a value $\lambda_{S'}$: this phenomenon is illustrated by the curve B of FIG. 3, again in respect of a given temperature.

Figure 4:
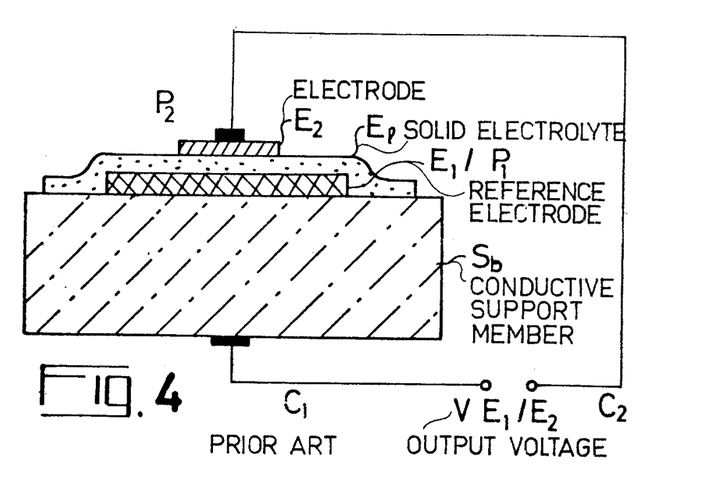
FIG. 4 is another sensor of the prior art comprising a reference electrode.

In order to provide a partial remedy for these drawbacks and in order to secure freedom from excessive dependence on temperature variations of the fluid mixture to be analyzed, a sensor structure has been proposed in which one of the electrodes also serves as reference medium. This structure can preferably be formed by the thin-film deposition technique since sensors of this type have a more rapid response. The sensor of FIG. 4 represents a general diagrammatic arrangement of this type of structure. The electrochemical cell is composed of a stack: electrode $E_1/P_1$, electrolyte $E_I$ and electrode $E_2$. This stack is deposited on a substrate $S_b$ so as to ensure mechanical rigidity of the assembly. In this instance, the substrate is a conductive support member which serves to establish an electrical connection between the conductor $C_1$ and the electrode $E_1/P_1$. The conductor $C_2$ is connected directly to the electrode $E_2$.

The electrode $E_1$ which is "buried" under the layer of electrolyte also serves as reference medium $P_1$. To this end, the electrode is fabricated in the form of a compound of the "metal/metal oxide" type.

In this case, we have the relations:

$$xM + \tfrac{x}{2} \rightleftharpoons M_xO \qquad (6)$$

$$\frac{|M^x|\,|O_2|^{\tfrac{1}{2}}}{|M_xO|} = K'(T) \qquad (7)$$

where M is the metal employed. Bearing in mind relation (4) which gives K(T), it is only necessary to find a value of K'(T) such that K(T)−K'(T)=constant in order to obtain temperature compensation over a wide range of concentration.

Figure 5:
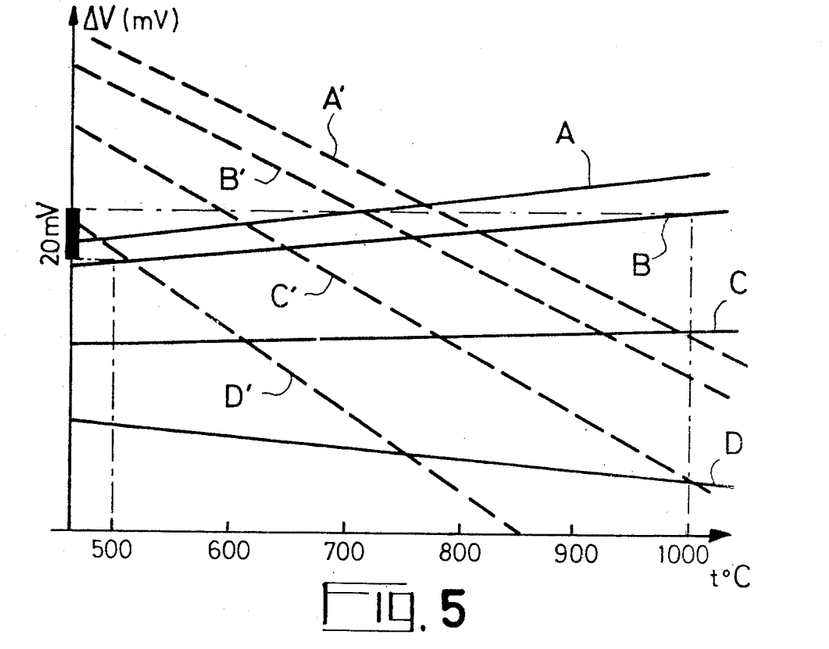
FIG. 5 is a set of curves for comparing the responses of the sensors of FIGS. 1 and 4.

FIG. 5 shows a double set of experimental curves: variation ΔV (in mV) of the response of a sensor as a function of temperature with the ratio of concentrations $CO/CO_2$ as a parameter. The curves A, B, C and D are those of a sensor of FIG. 4 with an electrode of the metal/metal oxide type or in other words which performs the function of reference medium; the curves A', B', C' and D' are sensors of FIG. 1 with, in respect of:

| | |
|---|---|
| A and A' | $\frac{CO}{CO_2} = 1$ |
| B and B' | $\frac{CO}{CO_2} = 0.5$ |
| C and C' | $\frac{CO}{CO_2} = 0.1$ |
| D and D' | $\frac{CO}{CO_2} = 0.01$ |

It is immediately apparent that a sensor of the type shown in FIG. 4 is much less dependent on temperature than a sensor of the type shown in FIG. 1, the tests having been performed under the same conditions.

For the analysis of a fluid medium having the above-mentioned composition $CO/O_2/CO_2$, the following associations can be employed for the construction of the electrode $E_1/P_1$=Ni/NiO, Pb, PbO, Pd/PdO, $Cr/Cr_2O_3$ although this enumeration is not exhaustive.

The sensor structures of FIG. 4 constitute an improvement over the prior art since they make it possible in particular to make the response of sensors more insensitive to variations in temperature of the fluid mixture to be analyzed and eliminate the difference in pressure between a reference medium $P_1$ which usually consisted of air at atmospheric pressure, and the medium $P_2$ to be analyzed; this pressure difference can be very considerable as in the analysis of exhaust gases, for example. However, the components of the cell remain exposed to direct aggressive action of the species of the fluid mixture, namely in a direction which is essentially normal to the plane of the electrodes of the electrochemical cell.

Figure 6:
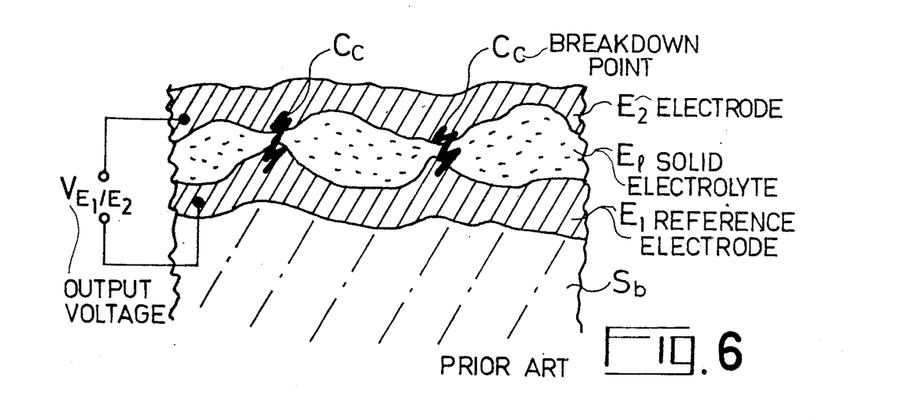
FIG. 6 is a detail view illustrating a particular defect of the sensor of FIG. 4.

Furthermore, structures of this type give rise to many problems relating to industrial manufacture. The top surface of the substrate $S_b$ (shown in FIG. 4) must in fact be perfectly smooth in order to ensure correct operation of the electrochemical cell, in which case it is difficult to ensure adhesion of the film which is deposited on said substrate. In the contrary event of surface irregularity of the substrate, this irregularity will be transmitted to the upper layers. In particular, the electrolyte layer may exhibit disparities in thickness such that electrical breakdown is liable to occur. In fact, at any point at which the electrolyte layer is too thin, the lowest values of mechanical and thermal stress are liable to produce short-circuits between $E_1$ and $E_2$. FIG. 6 illustrates this condition in which irregularities of structure are highly accentuated in order to gain a better understanding of the phenomenon. The possibilities of short-circuit are indicated by the reference CC. The other references are identical with those of FIG. 4.

In order to overcome these defects, the invention proposes an improvement in the construction of electrochemical sensors which, although specially adapted to a preferred sensor structure which will be described hereinafter, is generally applicable to the majority of structures of electrochemical sensors of the type comprising an electrode combined with the reference medium.

The principal distinctive feature which is common to all sensor structures according to the invention lies in the use of a reference electrode of the "metal/metal compound" type (M/MO, M/MF, M/M Cl and so forth). One face of said reference electrode is in contact with part of the solid electrolyte surface and all the other faces are protected from the fluid medium to be analyzed by a coating which is impervious to the species which are present in the fluid mixture: this imperviousness must be both chemical (gaseous diffusion) and electrochemical (ionic migration) as well as being inert with respect to all the chemical or electrochemical reactions which take place in the operation of the cell.

The assembly consisting of reference electrode and other components of the electrochemical cell can therefore be immersed in the medium to be analyzed and is no longer subjected to pressure differences such as pressure of medium to be analyzed/atmospheric pressure. Moreover, the reference remains perfectly stable by reason of its protection.

This improvement is equally applicable to cells which have either a massive solid electrolyte or an electrolyte deposited in the form of a thin film.

In the following description, consideration will be given by way of non-limitative example to the case of analysis of a gas mixture: $CO_2$, CO, $O_2$ (exhaust gas); the invention also applies to the case of analysis of non-reactive mixtures such as $N_2+O_2$.

Figure 7:
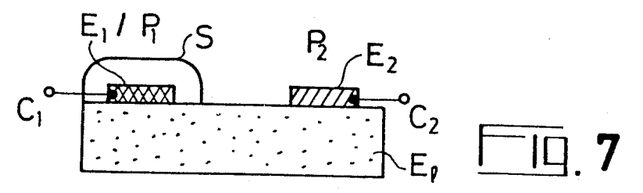
FIGS. 7 to 9 are sensors constructed according to a first approach of the invention.
Figure 8:
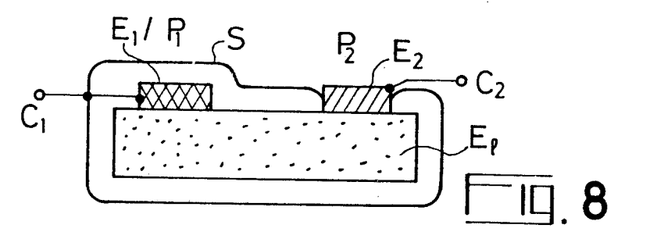
Figure 9:
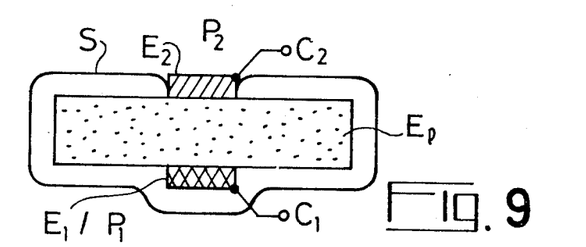

FIGS. 7 to 9 describe sensor structures according to the invention in which the electrochemical cell contains a massive electrolyte.

The electrochemical cell of FIG. 7 is composed of an electrode $E_1$ which also forms a reference $P_1$ such as an association Ni/NiO, for example. The inner face of said electrode is in contact with a solid electrolyte $E_l$, thus also ensuring mechanical rigidity of the complete assembly. The other faces of said electrode are protected from the external medium by an insulating inert substance S which is leak-tight and can consist of either enamel or alumina. Finally, the electrochemical cell is composed of an electrode $E_2$ of platinum, for example, the inner face of said electrode being in contact with the electrolyte $E_l$ and its top face being in contact with the medium $P_2$ to be analyzed. The usual techniques for limiting gaseous exchanges with the external medium can be employed, namely calibrated orifices, baffles, porous substances and so forth. The solid electrolyte $E_l$ can be formed of lime-stabilized zirconia or of other materials such as $Y_2O_3$, $Se_2O_3$ and so forth. The interelectrode potential difference is transmitted via the connections $C_1/C_2$ to any suitable detector. The electrochemical cell thus constructed is not subject to any danger of damage arising from pressure differences since it is completely immersed in the medium to be analyzed, is not provided with any seals which are difficult to apply in practice and the reference medium $P_1$ constituted by the electrode $E_2$ is perfectly stable since it is protected against any influence of the external medium.

It may also be advantageous to protect the electrolyte, for example with a view to increasing the service life of the reference electrode, since parasitic surface effects are liable to induce electron conductivity and to produce an ion current which may oxidize the reference electrode. A structure of this type is shown in FIG. 8 in which the same references as in FIG. 7 are again employed. The insulating substance S surrounds the entire cell except for the top face of the electrode $E_2$ which is in contact with the medium $P_2$ to be analyzed.

Finally, the improvement introduced by the invention is compatible with a structure of the type consisting of a stack $E_1$-$E_l$-$E_2$ as shown in FIG. 9. Since the electrolyte is massive, this structure is not subject to any potential danger of breakdown as was the case in the fault condition already mentioned with reference to FIG. 6.

Sensors comprising electrochemical cells fabricated in accordance with the thin-film technique can be preferred for certain applications since they have lower response inertia, are of smaller overall size and can be fabricated by means of conventional microelectronic techniques. In accordance with the aspect just mentioned, the sensors can in particular be intimately associated with other electronic components formed on the same substrate or on an adjacent substrate without being exposed to high temperatures in order to ensure correct operation of the electronic circuits. By way of example, the leads $C_1$/$C_2$ which are also formed by deposition can be connected to a threshold amplifier for detecting the point of inflexion of the curves shown in FIG. 2. This aspect, however, does not come within the scope of the invention.

It is also necessary to overcome the practical difficulties mentioned above and arising from the thin-film technique, especially the potential danger of short-circuits recalled in the foregoing. This can readily be achieved by adopting an arrangement of electrodes of the coplanar type which completely excludes such dangers since the thickness of the electrolyte no longer plays any part.

Figure 10:
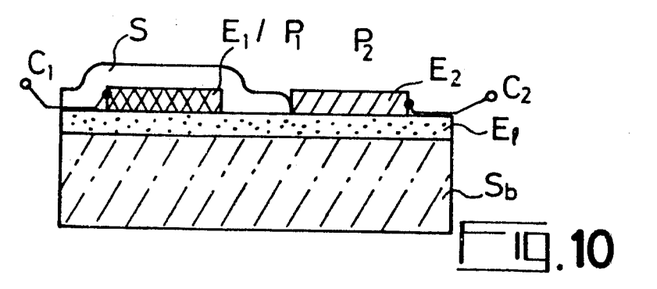
FIGS. 10 and 11 are sensors constructed according to a second approach of the invention.
Figure 11:
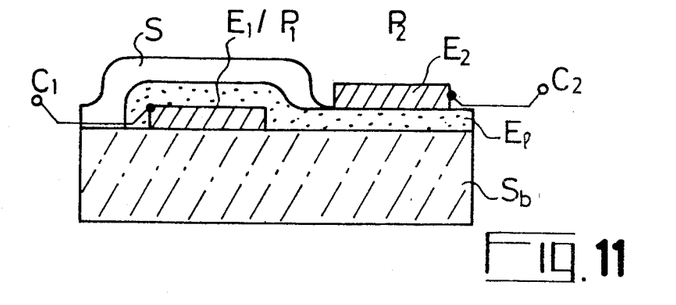

FIGS. 10 and 11 illustrate two alternative forms of structures according to the invention in the case of a sensor comprising an electrochemical cell which is fabricated by means of the thin-film technique. In both alternative forms, the electrochemical cell is deposited on an inert substrate $S_b$ which ensures mechanical strength and rigidity of the assembly. This substrate can be extended in any desired direction in order to be adapted to means for attachment to a casing.

In FIG. 10, the two electrodes are deposited on the solid electrolyte $E_l$ which is in turn deposited on the substrate $S_b$. The electrodes $E_1$/$P_1$ and $E_2$ are located in the same plane whilst the electrode spacing can be adjusted at will and no longer constitutes a critical parameter. Irregularities of the surface structure of the substrate no longer have any influence on good operation of the cell. The substrate can be formed of material having good insulating properties at the operating temperature of the device (corundum, for example).

According to the essential aspect of the invention, the electrode $E_1$/$P_1$ is protected from the external medium by means of an impervious and inert insulator S which covers said electrode. As in the case of the sensors shown in FIGS. 7 to 9, it is possible to employ an association of type Ni/NiO in order to fabricate this reference medium electrode. The electrode $E_2$ of platinum, for example, is in contact with the medium $P_2$ to be analyzed.

In FIG. 10, the electrodes $E_1$/$P_1$ and $E_2$ are located on each side of the solid electrolyte $E_l$. However, one electrode is always set back with respect to the other in order to prevent any effect of the "dielectric thickness" parameter. The electrolyte located above the reference electrode $E_1$/$P_1$ is covered by an insulator S.

In both cases, the leads $C_1$/$C_2$ can be formed by making use of a platinum lacquer so as to form on the substrate an outward extension of the electrodes from the cell and thus to provide the output connecting leads of the sensor. In the case of FIG. 11, the substrate $S_b$ can be electrically conductive and provides the connecting lead $C_1$.

Typical values are:
thickness of electrodes: 1000 $\overset{\circ}{A}$ to 100 $\mu$m
thickness of electrolyte: 1000 $\overset{\circ}{A}$ to 100 $\mu$m The deposits can be formed by well-known techniques such as vacuum deposition (cathodic sputtering, evaporation), deposition in vapor phase, electrochemical deposition or ionic implantation, or a combination of two or more of these techniques.

The usual and well-known methods of limitation of gaseous exchanges can be adopted for both types of sensor.

In the case of analysis of fluid mixtures away from the state of thermodynamic equilibrium, the sensors of FIGS. 10 and 11 and also those of FIGS. 7 to 8 are nevertheless attended by certain disadvantages which they share with sensors of the prior art. In fact, as indicated earlier, catalysis takes place while the fluid mixture to be analyzed passes through the electrode $E_2$ in the direction of its thickness. Catalysis must be as complete as possible and this makes it necessary to provide electrodes $E_2$ of relatively substantial thickness.

Other sensor structures have been proposed for ensuring good catalysis while permitting the use of electrodes which are deposited in a thin film. This is obtained by dissociating the catalysis function from the measuring electrode $E_2$.

Figure 3:
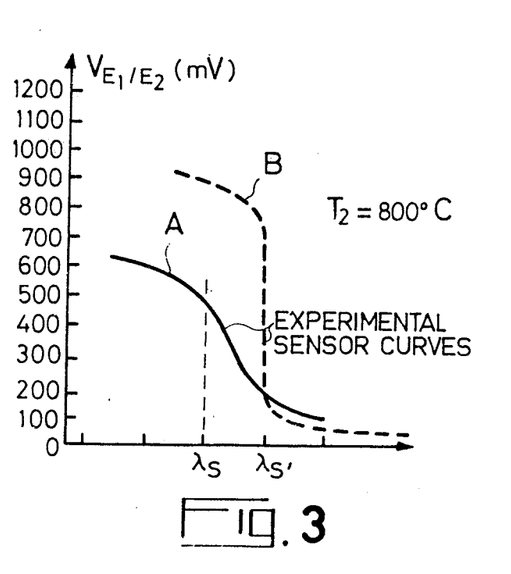
FIG. 3 illustrates certain defects of the sensor of FIG. 1 by means of curves.

As has already been noted, it should finally be mentioned in regard to curve B of FIG. 3 that inflexion of the response curves of the sensor is liable to take place at a different value of stoichiometry of the reaction. One reason for this lies in defective catalysis in sensors of the prior art (for example a catalytic process in which the fluid mixture to be analyzed passes through one of the electrodes in the direction of its thickness). Another reason lies in the fact that, in certain structures, the means employed for limiting gaseous exchange between the external medium in which the gas to be analyzed circulates and the interior of the sensor have the effect of selectively introducing a distortion in the velocity of diffusion (within the interior of the sensor) of the different species of the fluid mixture to be analyzed. Sensor structures which serve to control and utilize this phenomenon can be developed with a view to producing sensors for detecting ratios of relative concentrations of two reactive species of a fluid mixture to be analyzed which differ from a predetermined value of the stoichiometric ratio of the reaction.

Figure 12:
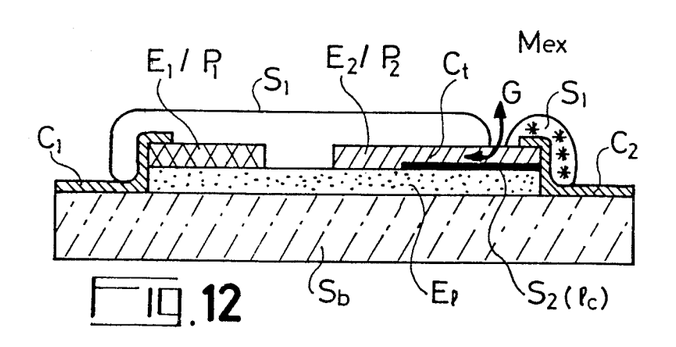
FIGS. 12 and 13 are preferred alternative embodiments of a sensor according to the invention.
Figure 13:
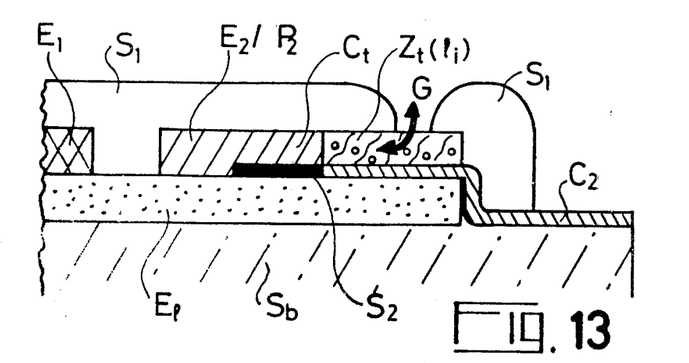

FIGS. 12 and 13 represent two preferred alternative sensor structures since they combine the advantages of the structures mentioned above with the advantages of the present invention and consequently remove practically all the disadvantages attached to sensors of the prior art, thus permitting the construction of reliable sensors which can be manufactured in large-scale production with a reasonably low proportion of rejects.

The sensor of FIG. 12 essentially differs from the sensor of FIG. 10 in the fact that the electrode $E_2$ has two zones and communicates directly with the medium $M_{ex}$ to be analyzed through an orifice G formed in the insulating substance $S_1$ which covers said electrode. In the first zone $C_t$, the bottom face of the electrode is separated from the electrolyte $E_l$ over a distance $l_c$ by means of an insulating substance $S_2$ of the same type as the substance $S_1$. The fluid to be analyzed is intended to pass through the substance $C_t$ which is a catalyst. In this zone, the reactive species of the mixture to be analyzed (for example CO and $O_2$ in the case of exhaust gases) are brought to full thermodynamic equilibrium before they reach the electrochemical cell proper: $E_2/P_2-E_l-E_1/P_1$. $P_2$ constitutes the real medium to be analyzed. In actual fact, the zone $C_t$ is only the extension of the electrode $E_2/P_2$ and is constituted by the same material such as platinum, for example, which is deposited in a thin film. Catalysis takes place by passing the fluid through the catalyst in a direction parallel to the plane of the electrodes and no longer by passing the fluid through the catalyst in the direction of its thickness. The electrodes are extended towards the exterior by the contacts $C_1$ and $C_2$ which can be formed of platinum lacquer. The coplanar structure of FIG. 10 is also shown in this figure; the other elements of the sensor are designated by the same references and will not be described further.

FIG. 13 is an alternative form of FIG. 12 and includes an additional means $Z_t$ consisting of a transfer impedance which extends over a predetermined length $l_i$. This transfer impedance is constituted by an inert porous body and is intended to modify, in pre-established proportions, the ratio of relative concentrations of the reactive species of the fluid mixture to be analyzed. In other words, the analysis is not carried out on the fluid mixture in the form in which this latter flows through the medium which is external to the sensor but in the form to which said mixture will be converted after passing through the transfer impedance. The object thus contemplated is to control the shift of the point $\lambda_s$, of curve B in FIG. 3. It is possible in particular to apply a sensor of this type to regulation of the air-fuel mixture in predetermined proportions. This application does not come within the scope of the invention and will not be further discussed here. There are again shown in FIG. 13 the two zones $C_t$ and $E_2/P_2$ of FIG. 12.

These two sensors can be placed directly within the medium to be analyzed. Traversal of the different zones: catalyst $C_t$, electrode $E_2/P_2$ (and the impedance $Z_t$ in the case of FIG. 13) is sufficient to produce a retarding action and to limit fluid exchanges between the external medium and the interior of the sensor.

Figure 14:
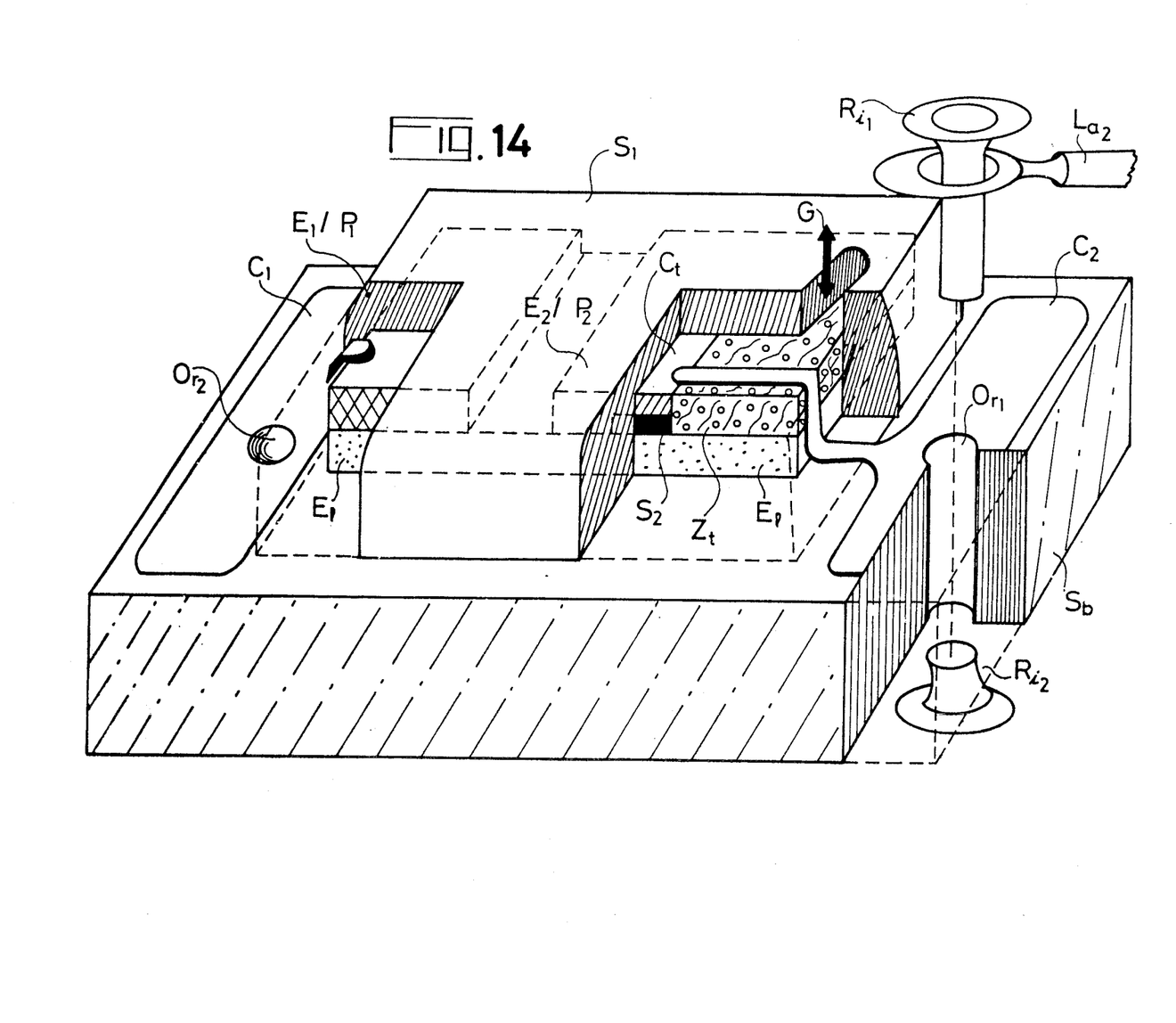
FIG. 14 is a view in perspective showing the sensor of FIG. 12.

The structure of the sensor of FIG. 13 is more fully illustrated in FIG. 14. In this figure, cuts have been made through the structure in order to show the arrangement of the different components of the sensor with greater clarity. The substrate $S_b$ can also serve to fix the sensor assembly within a casing. Orifices $Or_1$ and $Or_2$ have been formed at both ends through the substrate $S_b$ at the level of the metallic strips of the output contacts $C_1$ and $C_2$. The fastening means $Ri_1/R_2$ can also serve as contact terminals for establishing an electrical connection $La_2$ through which the sensor output signals are transmitted to the exterior. For the sake of enhanced clarity, only one fastening element has been shown in FIG. 14. The sensor of FIG. 12 can be represented in the same manner by dispensing with the zone $Z_t$.

Figure 15:
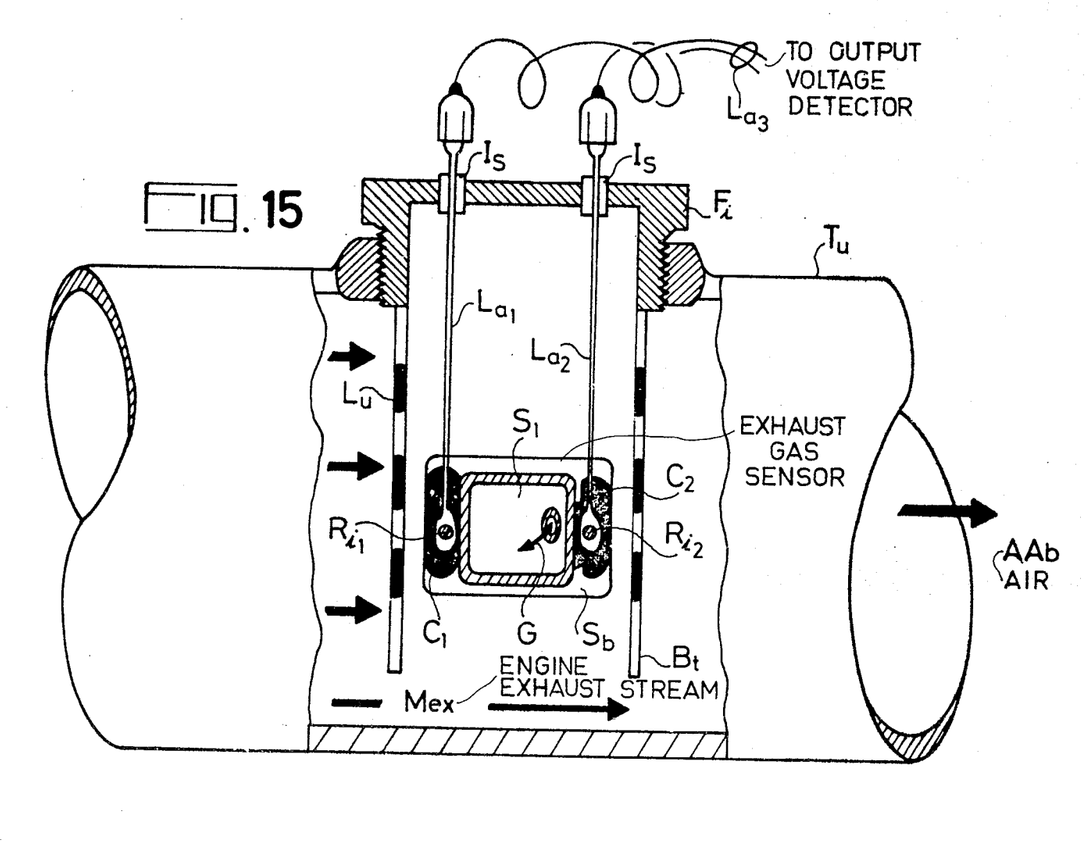
FIG. 15 illustrates the application of the sensors according to the invention to the analysis of the exhaust gases of an internal combustion engine.

A sensor designed in the manner which has just been described can be inserted in a casing and placed within the fluid mixture to be analyzed. A sensor within its casing $B_t$ as shown in FIG. 15 is employed for analyzing the composition of the exhaust gases of an internal combustion engine in which said gases flow within an exhaust pipe $T_u$ before being discharged into the atmosphere AAb. The casing can be screwed into the exhaust pipe. The sensor is attached by means of rigid connections $La_1$ and $La_2$ which traverse the head $F_t$ of the casing through two insulating terminals $I_s$. The electric signals collected are transmitted through connections $La_3$ to suitable electronic units for detecting inflexion of the curve about $\lambda_s$ (FIG. 2) or more generally $\lambda_s$, (FIG. 3). The casing $B_t$ offers an additional protection against direct aggressive action of exhaust gases. The need for this protection is not absolutely imperative. Unprotected sensors of the type shown in FIGS. 12 and 13 have been subjected to an endurance test cycle of 350 hours in an environment simulating an internal combustion engine without exhibiting any appreciable degradation from the point of view of either electrical characteristics or mechanical appearance.

The invention is not limited to the embodiments hereinabove described and in particular to any technological environment such as external geometry, mode of attachment, electric contacts, and has been described solely by way of illustration. Similarly, the applications which may be contemplated are not limited to analysis of exhaust gases of an internal combustion engine. In accordance with well-known practice, the different components of the sensor can be selected from a wide range of materials among which the following can be mentioned by way of example and without any limitation being implied:

the electrode $E_1/P_1$ can be constituted by one of the following associations: Ni/NiO, Pb/PbO, Ag/AgO, Pd/PdO or Cr/$Cr_2O_3$ or more generally by a system in which a metal is employed in combination with an element of Group VIIa of the periodic table of elements;

the electrode $E_2/P_2$ can be of platinum, gold or silver or of any alloy based on these metals;

the electrolyte can be of zirconia, thoria or cerium oxide stabilized by one or a number of elements of Groups IIa and IIIb of the periodic table;

the catalyst $C_t$ can be of platinum having either a compact or porous texture or else it can be constituted by an inert porous substance such as zirconia or alumina charged with catalyst, metal or metal oxide such as: ZnO, $CeO_2$, $MnO_2$, $Mn_2O_3$, $Fe_2O_3$, $CO_2O_3$, NiO, CuO, $Cu_2O$, $Cr_2O_3$, $TiO_2$, $V_2O_5$, $Ag_2O$ or PbO;

the transfer impedance $Z_t$ can be constituted by an inert porous substance such as zirconia or alumina;

the insulating materials can be constituted, for example, by dielectric enamels of the type usually employed by manufacturers of hybrid circuits or by other dielectric and inert layers deposited by thin or thick film techniques (in the sense usually understood in microelectronics);

the substrate can consist of good electrical insulating material which is inert with respect to all electrochemical reactions occurring in the operation of the sensor with high mechanical strength and good thermal adaptation. The best example is alumina in the form of a high-grade ceramic or preferably monocrystalline alumina of the corundum or sapphire type. Depending on the operating temperature of the sensor, other materials can be adopted such as quartz, certain metal oxides in ceramic or monocrystalline form or alternatively certain nitrides such as silicon nitride.

What is claimed is:

1. An electrochemical sensor for measuring the concentrations of species contained in a fluid mixture and comprising an electrochemical cell having a flat structure, said cell being constituted by a first partial-pressure internal reference electrode having one face either wholly or partly in contact with a solid electrolyte which is an ionic conductor for one of the species of said fluid mixture or for an ion which is capable of reacting with said species, and by a second electrode which communicates with the fluid mixture to be analyzed, one face of said second electrode being either wholly or partly in contact with said solid electrolyte, all the other faces of said first electrode abutting and being protected by an inert envelope and said envelope being impervious to the species which are present in said fluid mixture;

wherein said first electrode and said second electrode are both deposited on the same face or on opposite faces of said solid electrolyte and are so arranged with respect to each other such that the first electrode or the projection thereof in the plane of said second electrode is in adjacent relation to said second electrode.

2. An electrochemical sensor according to claim 1, wherein said solid electrolyte, said first electrode and said second electrode are formed by deposition on a substrate which ensures mechanical strength and rigidity of the electrochemical cell.

3. An electrochemical sensor according to claim 1 in which said second electrode is also divided into a plurality of functionally distinct zones, one face of a first zone being adapted to provide a contact with said solid electrolyte and one face of a second zone being adapted to communicate with said medium to be analyzed, wherein said second electrode is protected by an inert envelope abutting on all the other faces thereof, said envelope being impervious to the species which are present within the fluid mixture.

4. An electrochemical sensor according to claim 1, wherein said first partial-pressure internal reference electrode is constituted by a system comprising a metal and an oxide of said metal.

5. An electrochemical sensor according to claim 1, wherein said first partial-pressure internal reference electrode is constituted by a system comprising a metal and a combination of said metal with an element of group VIIa of the periodic table of elements.

6. An electrochemical sensor for measuring the concentrations of species contained in a fluid mixture and comprising an electrochemical cell having a flat structure, said cell being constituted by a first partial-pressure internal reference electrode having one face either wholly or partly in contact with a solid electrolyte which is an ionic conductor for one of the species of said fluid mixture or for an ion which is capable of reacting with said species, and by a second electrode which communicates with the fluid mixture to be analyzed, one face of said second electrode being either wholly or partly in contact with said solid electrolyte, all the other faces of said first electrode abutting and being protected by an inert envelope and said envelope being impervious to the species which are present in said fluid mixture;

wherein said electrolyte is provided with a sufficient thickness to ensure mechanical strength and rigidity of the electrochemical cell.

7. An electrochemical sensor according to claims 1 or 6, wherein said inert envelope further abuts and protects all surfaces of said electrolyte not contacting said first and said second electrodes.

* * * * *